United States Patent [19]
Bogert

[11] Patent Number: 5,853,393
[45] Date of Patent: Dec. 29, 1998

[54] CATHETER NEEDLE LOCKING AND CATHETER HUB UNLOCKING MECHANISM

[75] Inventor: David L. Bogert, Plainville, Conn.

[73] Assignee: Johnson & Johnson Medical, Inc., Arlington, Tex.

[21] Appl. No.: 483,951

[22] Filed: Jun. 7, 1995

[51] Int. Cl.[6] .................................................. A61M 5/178
[52] U.S. Cl. ......................... 604/165; 604/164; 604/198; 604/263
[58] Field of Search .................... 604/110, 164, 604/165, 171, 198, 263

[56] References Cited

U.S. PATENT DOCUMENTS

| | | | |
|---|---|---|---|
| 4,631,057 | 12/1986 | Mitchell | 604/198 |
| 4,790,828 | 12/1988 | Dombrowski et al. | 604/198 |
| 4,804,371 | 2/1989 | Vaillancourt | 604/198 |
| 4,826,490 | 5/1989 | Byrne et al. | 604/198 |
| 4,832,696 | 5/1989 | Luther et al. | 604/164 |
| 4,834,718 | 5/1989 | McDonald | 604/195 |
| 4,917,669 | 4/1990 | Bonaldo | 604/164 |
| 4,944,725 | 7/1990 | McDonald | |
| 4,950,252 | 8/1990 | Luther et al. | 604/198 |
| 4,952,207 | 8/1990 | Lemieux | 604/164 |
| 4,964,854 | 10/1990 | Luther | 604/166 |
| 4,978,344 | 12/1990 | Dombrowski et al. | 604/198 |
| 4,994,041 | 2/1991 | Dombrowski et al. | 604/164 |
| 5,051,109 | 9/1991 | Simon | 604/263 |
| 5,084,030 | 1/1992 | Byrne et al. | 604/198 |
| 5,205,829 | 4/1993 | Lituchy | 604/164 |
| 5,215,528 | 6/1993 | Purdy et al. | 604/164 |
| 5,300,045 | 4/1994 | Plassche, Jr. | 604/263 |
| 5,356,387 | 10/1994 | Sirbola | |
| 5,447,501 | 9/1995 | Karlsson et al. | 604/198 |
| 5,458,658 | 10/1995 | Sircom | 604/192 |
| 5,501,675 | 3/1996 | Erskine | 604/263 |
| 5,569,202 | 10/1996 | Kovalic et al. | 604/110 |

FOREIGN PATENT DOCUMENTS

| | | |
|---|---|---|
| WO 92 18182 | 10/1992 | European Pat. Off. . |
| WO 92 22344 | 12/1992 | European Pat. Off. . |
| 2 292 525 | 2/1996 | European Pat. Off. . |
| WO 95 23003 | 8/1995 | United Kingdom . |
| WO 93 054840 | 4/1993 | WIPO . |

*Primary Examiner*—John D. Yasko
*Assistant Examiner*—Cris L. Rodriguez
*Attorney, Agent, or Firm*—Joseph F. Shirtz

[57] ABSTRACT

A catheter needle tip protector and a safety mechanism which provides fail/save protection to clinical personnel against the possibility of accidental punctures by a used intravenous (IV) needle through the provision of automatic catheter needle tip protecting structure which becomes operative upon withdrawal of the needle from the body of a patient.

14 Claims, 5 Drawing Sheets

CATHETER NEEDLE LOCKING AND CATHETER HUB UNLOCKING MECHANISM

BACKGROUND OF THE INVENTION

1. Field of the Invention

The present invention relates, in general, to intravenous catheter insertion devices, and in particular relates to a catheter needle tip protector and a safety mechanism which provides fail/save protection to clinical personnel against the possibility of accidental punctures by a used intravenous (IV) needle through the provision of automatic catheter needle tip protecting structure which becomes operative upon withdrawal of the needle from the body of a patient.

Furthermore, the invention is also directed to a generally automatic needle tip guarding and catheter hub releasing mechanism which simultaneously covers the needle tip upon withdrawal from the body of a patient while enabling a catheter to remain in the site of the venipuncture, and releases a Luer lock lug located on the catheter hub when the cannula of the needle is fully retracted so as to place the needle tip into a fully guarded condition.

Pursuant to a further embodiment of the invention, there is also provided a catheter unlocking mechanism incorporating a tethering line, particularly with the utilization of a cannula or needle guard in the form of a bag or bellows for the receipt of the needle cannula, and incorporates a redundant system adapted to prevent a nose assembly of the cannula structure from separating from the cannula and exposing the latter and releasing the catheter hub prior to fully guarding the needle.

The utilization of clinical apparatus in which pointed hollow needles or cannulas are employed in order to puncture the skin of a patient, and especially catheters utilizing such needles to effectuate venipunctures, is well known in the medical art and is widely practiced by physicians and clinical personnel for the purpose of injecting fluids and drugs directly into the bloodstream of patients. Additionally, during surgical operations or procedures it may be frequently required that whole blood transfusions and parenteral fluids be administered to a patient undergoing such surgical procedures. Basically, as is well known and has been employed for a considerable length of time, the introduction of such fluids into the cardiovascular systems of patients has necessitated the forming of a venipuncture utilizing a hollow rigid needle having a proximal attachment site for a fluid connection which is adapted to interconnect the needle with a source of intravenously administered fluids.

The foregoing method of administering fluids to patients through venipunctures has been subject to some rather serious problems in the administration of fluids to patients in this medical technology. Thus, a primary concern which had to be addressed resided in the inherent rigidity of the needle, the latter of which is normally constituted of surgical-quality steel, and while inserted into the vein of a patient necessitated the needle to be maintained for reasons of safety in a fixed position at the general site of the venipuncture throughout the duration of fluid administration or transfusion, whereby such a procedure could conceivably consume a considerable length of time. In addition to the foregoing, at times it has been necessary to periodically draw blood samples and/or successively administer intravenous fluids to a patient, thus requiring the patient to be subjected to a series or plurality of venipunctures, each administered at a specific time and at different sites on the body, resulting in a relatively traumatic experience to the patient in view of such repeated and somewhat painful and unpleasant venipunctures.

In order to ameliorate or possibly even eliminate the foregoing problems, in the medical technology it has been more recently the practice to introduce a flexible tubular catheter of a low-friction material, such as a silastic or Teflon into the vein of a patient and to permit the catheter tube to remain in such a position over lengthier periods of time for purposes of; for example, periodically administering fluids, including parenteral fluids, blood/plasma transfusions, medications in liquid form and also for the collection of blood samples and the like. In this manner, the previously encountered trauma, extravasation, and infiltration caused by repeated venipunctures have been largely avoided, and the danger and discomfort to a patient of leaving a rigid needle in the body for a prolonged period of time has been generally overcome. Thus, in order to position the distal end of such a flexible catheter tube within the body cavity of a patient, such as a vascular cavity or vein, there is normally employed a cannula or hollow sharp-tipped needle for the purpose of forming the venipuncture. Thereafter, the flexible catheter tube, which is telescopically and slidably coaxially mounted on the outer circumference of the cannula or hollow needle so as to extend sleeve-like thereabout is advanced along the length of the needle into the vein subsequent to the needle having formed the venipuncture. Thereafter, the needle is adapted to be withdrawn from the interior of the catheter tube, while permitting the latter to remain within the body of the patient at the site of the venipuncture, and the needle is suitably discarded.

Inasmuch as the needle which has been previously positioned in the body of the patient upon forming the venipuncture may have been exposed to infectious agents; for instance, such as a patient infected with the Acquired Immune Deficiency Syndrome (AIDS) which is frequently or practically always ultimately fatal in nature, or other dangerous infectious conditions such as hepatitis, there is present the danger or hazard that the clinical personnel may inadvertently or accidentally jab or stick themselves with the used needle after withdrawal from the body of the patient, with the possibility of infection or even death resulting therefrom.

Although numerous prior art publications are devoted to the development and disclosure of devices for protecting physicians or clinical personnel from harm caused by accidental injuries through sticking themselves with needles withdrawn from the bodies of patients, difficulties have been encountered in producing the devices in which the withdrawal of a needle from a patient's body and separation of the catheter therefrom concurrently automatically activates a protective needle-guarding mechanism. Moreover, pursuant to a particular aspect, it is also desirable that concurrently or simultaneously with the retraction of the used cannula or needle tip portion into a confined or guarded area by means of which there is assured the safety of the clinical personnel, there is also automatically effectuated an unlatching or disconnecting action of the catheter hub from a locking structure which attaches the needle assembly to the catheter.

2. Discussion of the Prior Art

In a particular instance, U.S. Pat. No. 4,631,057 to Mitchell discloses a guard tube adapted to slide forwardly in order to protect the pointed end of a hypodermic needle from accidental contact by clinical personnel subsequent to usage. However, the mechanism disclosed therein, similar to the current state of the art is only effective if the clinical personnel remembers to push the guard tube into its effective position subsequent to the performing of an injection. This leaves open the possibility that this step may upon occasion be forgotten and may conceivably lead to injury and possible fatal results to the physician or clinical personnel.

In view of the foregoing, it is important to ensure provision of a safety mechanism which provides fail/safe protection to clinical personnel engaged with administering such venipunctures to patients; in effect, without requiring the need for any conscious forethought on the part of the clinician operating the device, and which will automatically protect the pointed end of a needle from projecting and accidentally sticking clinical personnel from the moment the needle is withdrawn from the body of a patient, while maintaining a connection with the catheter until the needle is safely contained.

McDonald U.S. Pat. No. 4,944,725 addresses the problem in disclosing an intravenous catheter which incorporates a structure for protecting a clinician or physician from accidental puncture which may result in the transfer of potentially dangerous infections to such personnel from the patient. The catheter is introduced into the patient's body with the aid of a sharp-tipped needle of hollow or cannular construction which is thereafter withdrawn from the patient's body into a protective housing in the absence of exposing the needle during any intermediate stage of the withdrawing process. The housing is then latched in place subsequent to needle withdrawal, and unlocking of a catheter hub of the tubular catheter in place subsequent to the time, while needle withdrawal and locking is carried in one continuous motion.

Another mechanism which is adapted in providing for protection of clinicians from being stuck by the point of a needle or cannula subsequent to or during removal thereof from the body of a patient is disclosed in Dombrowski et al. U.S. Pat. No. 4,790,828, wherein a nose or cap portion through which the needle extends is tethered to a housing by means of a collapsible tethering structure encompassing the needle. Subsequent to use, the needle is adapted to be retracted into a sheath-like axially expanding arrangement which will assuredly prevent potential injury to clinical personnel caused by being jabbed or stuck by the exposed tip or point of the used needle. Although this provides an improvement over the current state of the art relative to protection from needle sticking, Dombrowski et al. requires a frictional engagement of the components in order to be operative, which frequently renders the operation of the device rather difficult and not totally reliable in nature.

SUMMARY OF THE INVENTION

Accordingly, there is provided an improved and novel structure in the formation of a cannula or needle-tip protector, and particularly in the arrangement of a safety mechanism adapted for an essentially simultaneous guarded needle locking and catheter hub unlocking actuation upon withdrawal of the needle or cannula from the catheter. Another embodiment of a catheter unlocking device includes an extendable tethering line for triggering a needle guarding arrangement; in which the needle guarding mechanism which prior to extension of the tethering line, retains the catheter hub locked to the guarding mechanism. The cannula extends through the catheter hub and through a latching element having a central aperture for receiving the cannula so as to maintain a locking engagement between a Luer lock lug on the catheter hub, and a nose portion of a needle guarding housing through which the cannula extends forwardly so as to be adapted to be inserted into the vein of a patient. Upon withdrawal of the needle or cannula from the body of the patient, while permitting a catheter, such as a flexible tubular member encompassing the cannula to be slid forwardly in order to remain in position within the punctured vein of the patient, as the cannula is retracted from the aperture in the preferably plastic latching element, the latter in view of an inherently incorporated biasing or resilient action and its construction, disengages from the Luer lug on the catheter hub while concurrently laterally displacing the aperture from which the needle has been retracted so as to form an obstruction against any protuberance of the needle tip or cannula from the housing. This particular action simultaneously enables the separation of the housing and of the guarding structure encompassing the used needle or cannula arrangement and detachment therefrom of the catheter hub.

Pursuant to another embodiment of the invention, the plastic latching element may be tethered by means of a so-called "fishline" to the catheter hub and at the opposite end thereof to a housing including either a bellows or folded bag, with the needle being extended through the latching element as described hereinabove, whereby extension of the tether exerts an unlatching pull on the catheter hub.

Pursuant to a further embodiment of the invention, a thin flexible bag may form the extension covering the retracted needle, the latter of which may be tethered to the housing and nose guard portion through the intermediary of a looped flexible material.

Accordingly, it is an object of the present invention to provide a novel and unique mechanism for the simultaneous locking of a needle in a retracted guarded position and unlocking a catheter hub structure through a simple actuation of a latching element.

Another object is to provide a device or mechanism of the type described herein in which the latching element is interconnected to a housing at one end and to respectively a catheter hub at an opposite end through the intermediary of a tethering line, enabling the simultaneous unlatching of the catheter hub from the housing and retraction of the used needle tip into a flexible bag or similar guarding component responsive to extension of the tethering line.

BRIEF DESCRIPTION OF THE DRAWINGS

The foregoing and other objects of the invention and advantages are described herein in further detail hereinabove, taken in conjunction with the accompanying drawings; in which.

DETAILED DESCRIPTION OF PREFERRED EMBODIMENTS

Figure 1:
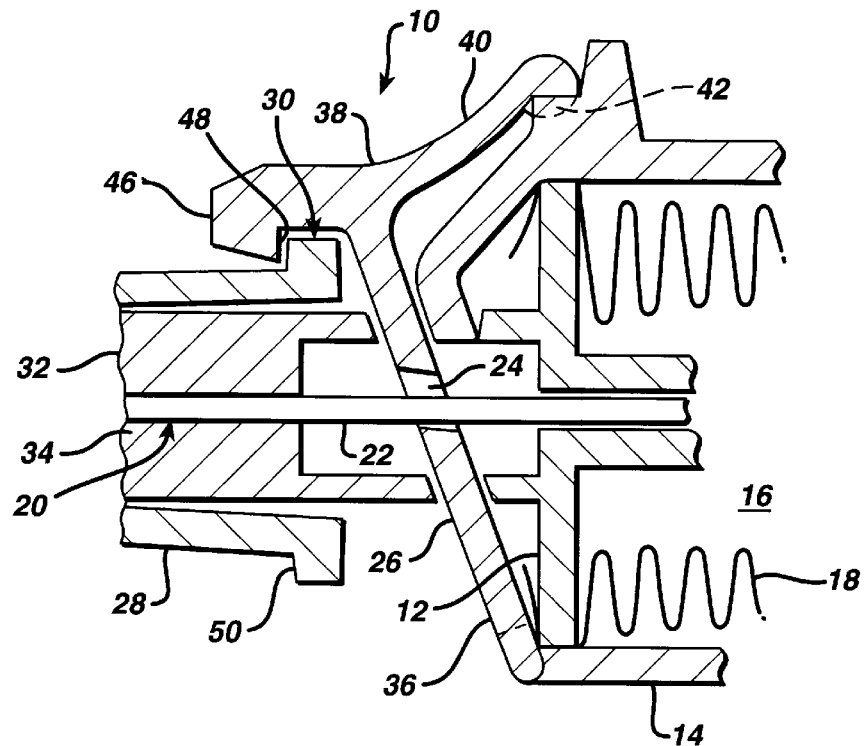
FIG. 1 illustrates, generally diagrammatically, a fragmentary sectional view through a needle locking and catheter hub unlocking mechanism pursuant to the invention, shown in a first locked and needle-extended position thereof.

Referring now in detail to the invention, particularly as disclosed in the embodiment of FIGS. 1 through 5 of the drawings, and especially as shown in FIG. 1, there is disclosed a needle locking and catheter hub unlocking mechanism 10. The leading or forward end 12 of a needle or cannula guarding housing 14 includes a cavity 16 containing a bag or a bellows 18, shown in a folded-together or compressed condition. Extending centrally and forwardly out from the housing 14 through a guide sleeve 20 is a cannula or hollow needle 22 adapted to form a venipuncture in a patient, and which also passes through a central aperture 24 formed in a latching element 26 constructed pursuant to the invention. The extended cannula 22 then passes through a catheter hub 28 possessing a Luer lock lug structure 30, which encompasses a nose piece 32 and gasket 34 contained therein. The leading end of the cannula or hollow needle 22 is adapted to be introduced into the body of a patient (not shown) for imparting a venipuncture for the administering of suitable fluids introduced through a catheter (not shown) encompassing and advanced into the puncture along the outer surface of the cannula (not shown). The catheter may be a flexible tubular member terminating at one end in the catheter hub 28, as is well known in the technology, and upon forming of the venipuncture by the tip of the cannula or hollow needle 22 is adapted to be slipped forwardly thereover into the patient while the needle or cannula 22 is adapted to be retracted from the catheter into the protective housing 14.

Figure 5:
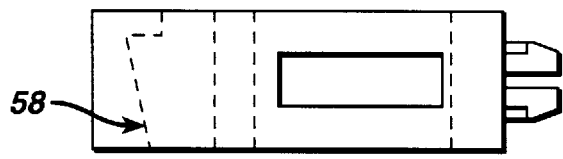
FIG. 5 illustrates a top plan view of the latching element of FIG. 3.
Figure 3:
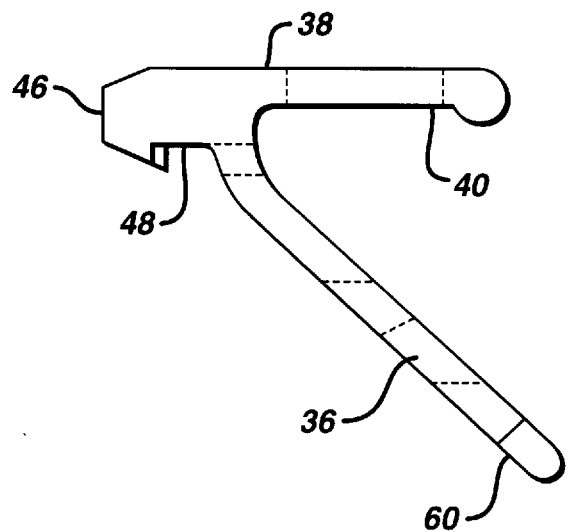
FIG. 3 illustrates a side view of the latching element of the mechanism in FIG. 1.
Figure 4:
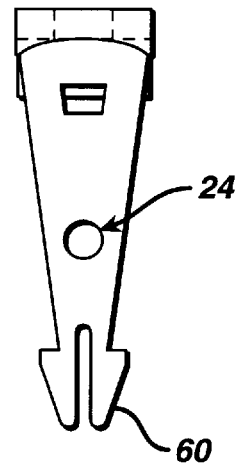
FIG. 4 illustrates an end view of the latching element of FIG. 3.

The latching element 26 for the needle locking and catheter hub unlocking mechanism, as shown in FIGS. 3 to 5, comprises a lever-shaped member having a central plate portion 36 having the aperture 24 through which the cannula 22 is inserted to project forwardly during the locked condition of the components; with the plate portion 36 being located at an incline with one forwardly extended end of the plate portion 36 including a T-shaped structure 38. One arm 40 of the T-shaped structure engages a protruding tab arrangement 42 on the front surface of the housing 14 containing the folded or compressed bag or bellows; whereas the other arm 44 of the T-shaped structure 38 includes a hook-like projection 46 forming a recess 48 into which there engages a lug 50 of a Luer lock forming an integral component of the catheter hub 28 so as to maintain the components in their interlocked condition as shown in FIG. 1 of the drawings.

Figure 2:
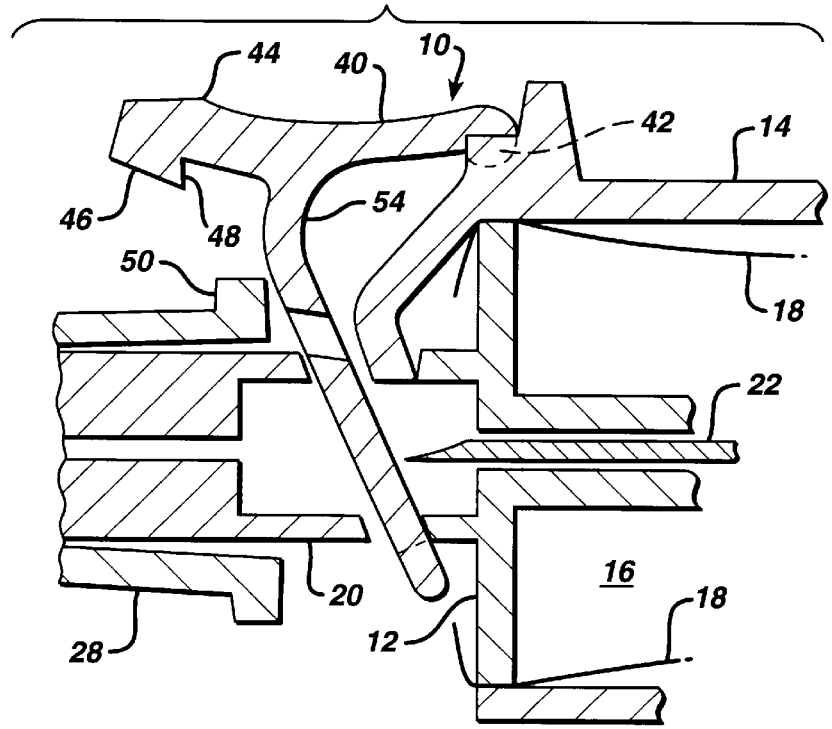
FIG. 2 illustrates a view similar to FIG. 1 with the mechanism being illustrated in the needle retracted and catheter hub unlocked condition.

Upon the venipunctural insertion of the tip portion of the needle or cannula 22 into the body of the patient and the sliding forwardly thereover of the flexible tubular catheter into the site of the puncture, the cannula 22 is retracted, as shown in FIG. 2 of the drawings, while leaving the catheter in place.

As the cannula 22 is retracted from the catheter through the central aperture 24 in the plate portion 36 of the latching element 26 for the catheter hub 28, the spring or biasing action of the plastic material of the T-shaped structure causes it to pivot or bend at location 54 so as to cause the aperture 24 to be displaced upwardly and the plate portion 36 forming a barrier preventing the tip of the retracted cannula 22 from extending beyond the nose guard portion of the housing. Simultaneously, the bending action of the plate portion 36 disengages the Luer lug 50 from the recess 48 in the opposite arm 44 of the T-shaped element, resultingly releasing the catheter hub 28 and thereby enabling the cannula components and guard housing 14 with the retracted cannula therein and the attached needle locking and catheter hub unlocking mechanism to be removed so as to provide for the capability of connecting a cooperating Luer lock structure (not shown) to the catheter hub 28 enabling the administering of parenteral fluids, blood or medications to the patient through the catheter in the venipuncture which remains attached to the catheter hub 28.

The mechanism 10 comprising the T-shaped plate element, as shown in FIGS. 3 through 5 of the drawings, includes a lip 58 having the recess 48 formed therein for retaining the Luer lock lug 50 and with the distal end 60 of the plate portion 36 member which includes the aperture 24 for the passage therethrough of the cannula 22 including a snap tab 60 which will prevent the plate 36 from completely popping free and falling off upon release caused by the withdrawal of the tip of the needle. This structure essentially provides a secure guarding mechanism for the cannula 22 needle and retains the catheter hub 28 secured thereto until after the guarding mechanism comprising the T-shaped element 38 is securely positioned over the tip of the withdrawn cannula 22. The mechanism simultaneously releases the catheter hub 28 and guardingly covers the tip of the used cannula 22, possibly generating a loud "click" noise to provide audio indication that the cannula is secured against external contact and the catheter components are separated therefrom.

The elements forming the mechanism 10 may be constituted of suitable plastic material, such as acetyl or the like, and essentially forms a so-called "trigger" upon the tip of the retracted cannula 22 clearing the cannula aperture 24 formed in the plate-shaped portion 36 of the mechanism, simultaneously guarding the retracted cannula and releasing the catheter hub 28.

Figure 6:
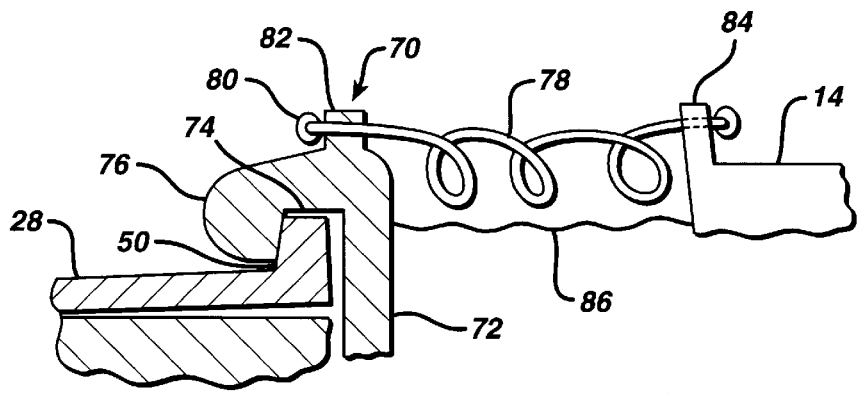
FIG. 6 illustrates, generally diagrammatically, a second embodiment of a needle locking and catheter hub unlocking mechanism pursuant to the invention shown in the interconnected locked condition thereof.
Figure 7:
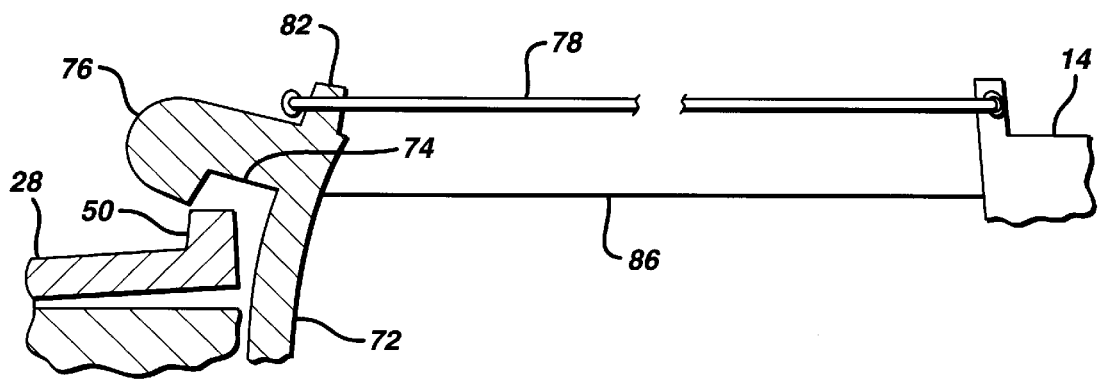
FIG. 7 illustrates the mechanism of FIG. 6 in the unlocked and needle retracted condition.

Referring to the diagrammatically shown embodiment of FIGS. 6 and 7 of the drawings; wherein similar elements as in FIG. 1 are identified by the same reference numerals; in essence, the mechanism 70 for disengaging the catheter hub 28 from the housing 14 may also be constituted of a plastic plate-shaped component 72 having a recessed hook portion 74 at one end 76, and wherein the plastic material is of a resilient formable nature. The hook portion 74 is interconnected to the catheter hub by means of engaging over a Luer lock lug 50 through a so-called "fishline" or coiled tether 78 attached at 80 to a projection 82 on component 72, and at an opposite end to a flange 84 on the housing 14 device. The tether 78 is essentially in a loosely coiled position in the extended-needle condition, and when the cannula 22 is retracted, with a cannula guard comprising a folded bag or compressed bellows 86 located between the housing 14 and a guard nose being fully extended so as to cause the needle tip of the cannula to be withdrawn therein, the resultingly extended "fishline" tether 78 deforms or bends the component 72, so as to release the Luer lock lug 50 on the catheter hub 28, as shown in FIG. 7, enabling the catheter hub 28 to be separated from the cannula assembly comprising the housing 14 and the mechanism 78 and 72. The used cannula 22 is contained within the extended bag or bellows, and thus secured and guarded against potential contact by a physician or clinical personnel.

Figure 8:
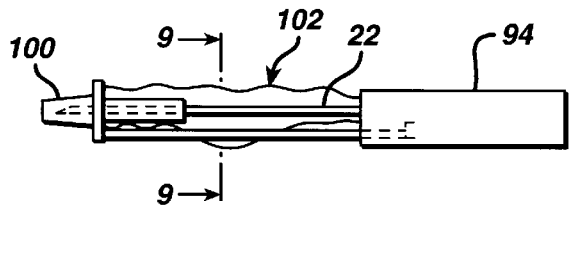
FIG. 8 illustrates, generally diagrammatically, a further embodiment of a catheter guard tethering device.
Figure 9:
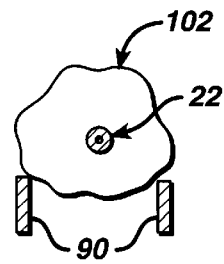
FIG. 9 illustrates a sectional view, on an enlarged scale, of the device of FIG. 8 taken along Line 9—9 in FIG. 8.
Figure 10:
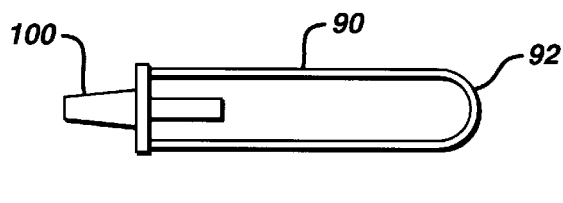
FIGS. 10 and 11 illustrate, respectively, plan and side views of the tethering structure utilized in the device of FIG. 8.

As shown in the embodiment of FIGS. 8 through 10 of the drawings, which is somewhat similar to that of FIGS. 6 and 7, a thin pair of tethers 90 form a single loop member 92 constituting two legs of a loop interconnects a housing 94 and a catheter hub with a Luer lock lug. Attached to the components extending between the housing 94 and a nose or guard member 100 is a thin flexible bag 102 which, upon retraction of the cannula 22, incorporates a guard for the retracted cannula and its needle tip.

Hereby, the device forming the tether may be of a thin-walled structure, as shown in FIG. 9, which as attached offset from a central axis will prevent rotation or torqueing between the components during operation, in effect, prevent rotation of the nose/guard member 100 relative to the housing 94 while firmly anchoring the former to the latter.

Figure 11:
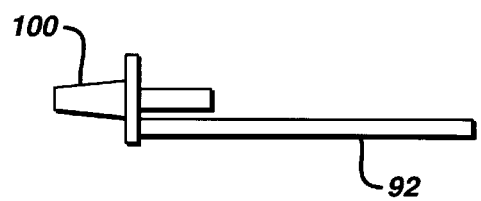

As shown in FIGS. 10 and 11, the tethers 90 forming the two legs of a loop 92 may be manufactured by molding, stretching and orienting techniques to produce a very strong linearly-oriented plastic material tether. Various plastics, including polyolefins and nylons readily lend themselves to this particular molding technique.

The tether is adapted to be attached to the housing 94 and, respectively the nose/guard member 100, and folded into a compartment beneath the housing.

Figure 12:
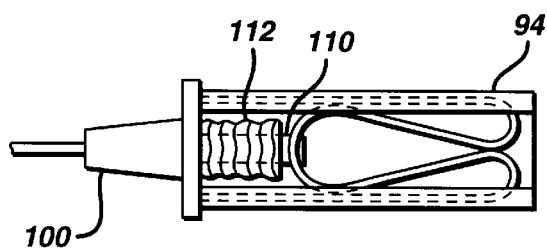
FIG. 12 illustrates, generally diagrammatically, a longitudinal sectional view of a modified embodiment of a tethering structure.
Figure 13:
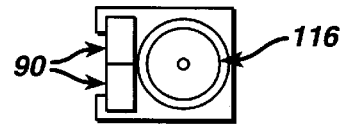
FIG. 13 illustrates an end view of the tethering structure of FIG. 12.

Particularly as shown in FIG. 12 of the drawings, illustrating a tether hold-down structure 110 connected to a compressed bag or tube 112 in the housing, this evidences that the tether may be coiled together in position below a blood chamber 116, as shown in the representation of FIG. 13 of the drawings.

Figure 14:
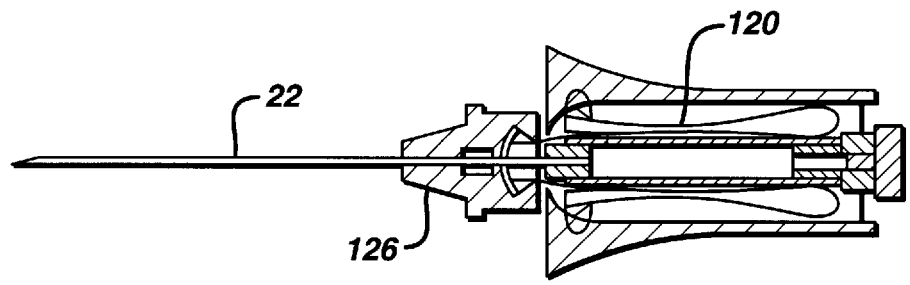
FIGS. 14 and 15 illustrate, respectively, two operative positions of a modified embodiment of a tethering and guard device for a catheter and cannula arrangement constructed pursuant to the invention.
Figure 15:
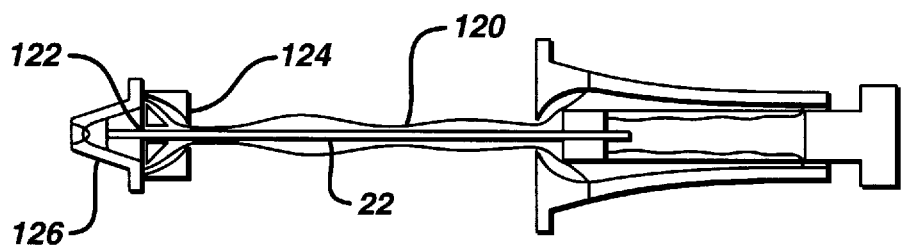

Pursuant to the schematically represented embodiment of FIGS. 14 and 15, this shows a somewhat modified structure of the arrangement of FIG. 12, whereby in this instance, the tether 120 may be a mylar or film strip having a hole 122 formed in the center thereof to enable passage therethrough of the cannula 22, the latter of which extends through a needle tip protector 124 and Luer lock 126, and upon cannula retraction causes the mylar strip to be biased towards the cannula by both the needle tip protector and the housing components in order to maintain itself alongside the cannula, as the cannula traverses the tip protector during retraction.

As illustrated, the attachment of the mylar strip may be mechanical in nature, such as by a snap fit, heat staking or other standard means of attachment. The particular use of two strips of mylar also prevents or resists torqueing or rotation of the needle tip protector relative to the housing portion of the arrangement.

From the foregoing, it becomes readily apparent that the invention is directed to novel and unique mechanisms for simultaneously locking a cannula and unlocking a catheter hub while providing for protection for a retracted cannula.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A cannula locking and catheter hub unlocking mechanism for a catheter insertion device, comprising:
   (a) a housing having a cannular needle received by said housing, said cannular needle extending from an end of said housing and being adapted to administer a catheter to a patient;
   (b) catheter hub supporting structure adjacent said housing and movable along said cannular needle and encompassing a portion of the cannular needle and defining an opening therein;
   (c) a catheter slideably mounted on said cannular needle, said catheter including a catheter hub engaged on said catheter hub supporting structure; and
   (d) means for locking said catheter hub to said catheter hub supporting structure in the extended operative position of said cannular needle and for releasing said catheter hub in the retracted position of said cannular needle while concurrently forming protective barrier against the tip of said retracted cannular needle being in an exposed condition, wherein said locking means comprises a plate element extending through said opening defined by said catheter hub supporting structure, said plate element including a central aperture whereby said cannular needle passes through said aperture in the extended operative condition and maintains said plate element in a catheter hub locking condition on said catheter hub supporting structure wherein there is a tab on said housing and said plate element has opposite extending arm portions at one end; one said arm portion being hingedly connected to said tab, and another of said arm portions including means for clampingly engaging said catheter hub.

2. A mechanism as claimed in claim 1, wherein at least a portion of said plate element is resiliently deformable whereby withdrawal of said cannular needle from said central aperture imparts a pivoting motion to said plate element causing said means at said other arm end to disengage from said catheter hub to enable said catheter to be detached from said device.

3. A mechanism as claimed in claim 2, wherein the pivoting motion of said plate element displaces the central aperture relative to the axis of the retracted cannular needle so as to form a protective barrier against external contact with said retracted cannular needle.

4. A mechanism as claimed in claim 1, wherein said clamping means on the other of said arm portions of said plate element comprises a recess, and there is a locking lug means included on said catheter hub being engageable in said recess.

5. A mechanism as claimed in claim 4, wherein said locking lug means comprises components of a Luer lock fitting.

6. A mechanism as claimed in claim 1, wherein said plate element is constituted of a plastic material.

7. A mechanism as claimed in claim 1, wherein extendable connecting means interconnects said catheter hub locking means and said housing, whereby displacement of said housing from said locking means causes said cannular needle to retract and said connecting means to extend so as to disengage said locking means from said catheter hub.

8. A mechanism as claimed in claim 7, wherein said connecting means comprises a tethering line having opposite ends attached to respectively said locking means and said housing.

9. A mechanism as claimed in claim 7, wherein said catheter hub has a locking lug means and said locking means comprises a resiliently deformable plate member, and a recess formed at one end of said plate member for latchingly engaging said lug means on said catheter hub.

10. A mechanism as claimed in claim 9, wherein extension of said connecting means deflects said plate member to enable said locking lug means to disengage from said recess and release said catheter hub from said device.

11. A mechanism as claimed in claim 7, wherein a bag or collapsible bellows extends between said housing and said locking means and encompasses said retracted cannular needle upon extension of said locking means.

12. A mechanism as claimed in claim 7, wherein a nose guard is tethered to said housing; and a bag or collapsible bellows extends between said nose guard and said housing for encompassing the retracted cannular needle.

13. A mechanism as claimed in claim 12, wherein a pair of parallel extending strips form a tether between said nose guard and said housing.

14. A mechanism as claimed in claim 13, wherein said strips are portions of a hooped tether.

\* \* \* \* \*